United States Patent [19]
Doherty et al.

[11] Patent Number: 5,322,504
[45] Date of Patent: Jun. 21, 1994

[54] METHOD AND APPARATUS FOR TISSUE EXCISION AND REMOVAL BY FLUID JET

[75] Inventors: Rex E. Doherty, Orinda, Calif.; E. Larry Hicks, Lilbum; Ray Gillies, Cumming, both of Ga.

[73] Assignee: United States Surgical Corporation, Norwalk, Conn.

[21] Appl. No.: 879,879

[22] Filed: May 7, 1992

[51] Int. Cl.$^5$ ............................................. A61B 17/22
[52] U.S. Cl. .................................. 606/167; 606/107; 604/22; 83/53; 83/177
[58] Field of Search ............................ 604/22, 27, 35; 606/107, 167, 159; 83/53, 177

[56] References Cited

U.S. PATENT DOCUMENTS

| | | | |
|---|---|---|---|
| 3,930,505 | 1/1976 | Wallach | 606/107 |
| 4,857,047 | 8/1989 | Amoils | 604/902 |
| 4,878,900 | 11/1989 | Sundt | 604/902 |
| 4,915,691 | 4/1990 | Jones et al. | 604/902 |
| 5,013,300 | 5/1991 | Williams | 604/902 |
| 5,037,431 | 8/1991 | Summers et al. | 606/167 |
| 5,037,432 | 8/1991 | Molinari | 604/35 |
| 5,097,731 | 3/1992 | Vives et al. | 83/53 |
| 5,135,482 | 8/1992 | Neracher | 604/22 |
| 5,135,484 | 8/1992 | Wright | 604/22 |
| 5,165,602 | 11/1992 | Arnout et al. | 83/177 |

FOREIGN PATENT DOCUMENTS

| | | | |
|---|---|---|---|
| 175096 | 3/1986 | European Pat. Off. | 604/35 |
| 3715418 | 11/1987 | Fed. Rep. of Germany | 606/128 |
| 6113 | 7/1989 | PCT Int'l Appl. | 606/167 |
| 9005493 | 5/1990 | PCT Int'l Appl. | 604/22 |

*Primary Examiner*—Ralph Lewis
*Attorney, Agent, or Firm*—Harris Zimmerman

[57] ABSTRACT

A method and apparatus for the excision and removal of tissue, such as the lens of the eye includes a pencil-like handpiece having a cannula probe extending from the distal end thereof. The probe includes an inner jet tube to direct a high pressure jet of fluid toward a tissue target, and an outer concentric aspiration tube to aspirate and remove fluid and tissue. The jet tube is recessed proximally within the concentric aspiration tube, and the aspiration tube has an end area significantly larger than the end area of the jet tube. These factors cooperate so that the negative pressure exerted by the aspiration tube creates a suction force that offsets and exceeds the force of the fluid jet. The jet tube is connected to a fluid pressure system including a positive displacement pump, a pressure regulator, safety release, control valve, and a pulse former. The jet tube emits pulses of high pressure fluid that impinge reiteratively on the target, creating shock waves that fracture and emulsify the lens tissue, and the fluid also acts as a solvent to transport the emulsified tissue into the aspiration tube. The handpiece also includes a vacuum bypass port disposed to be selectively occluded by a finger of the surgeon, so that vacuum pressure may be released immediately when needed.

7 Claims, 4 Drawing Sheets

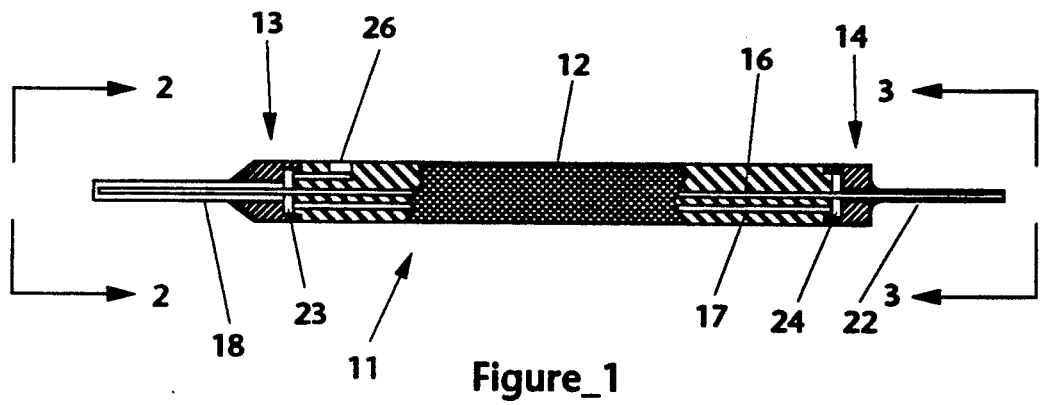
Figure_1
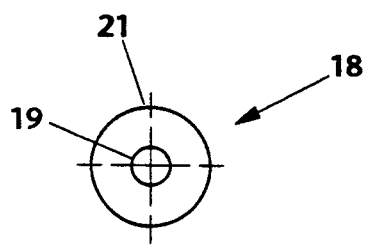
Figure_2
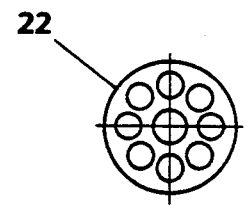
Figure_3
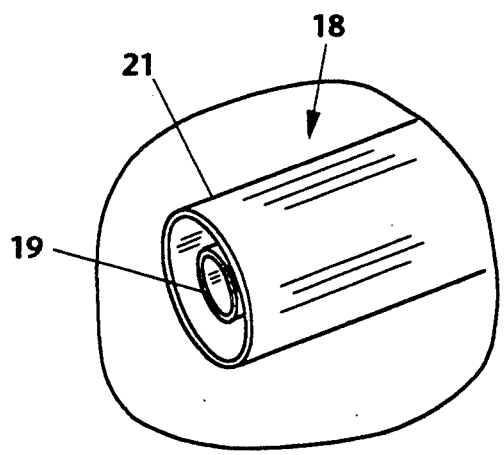
Figure_4

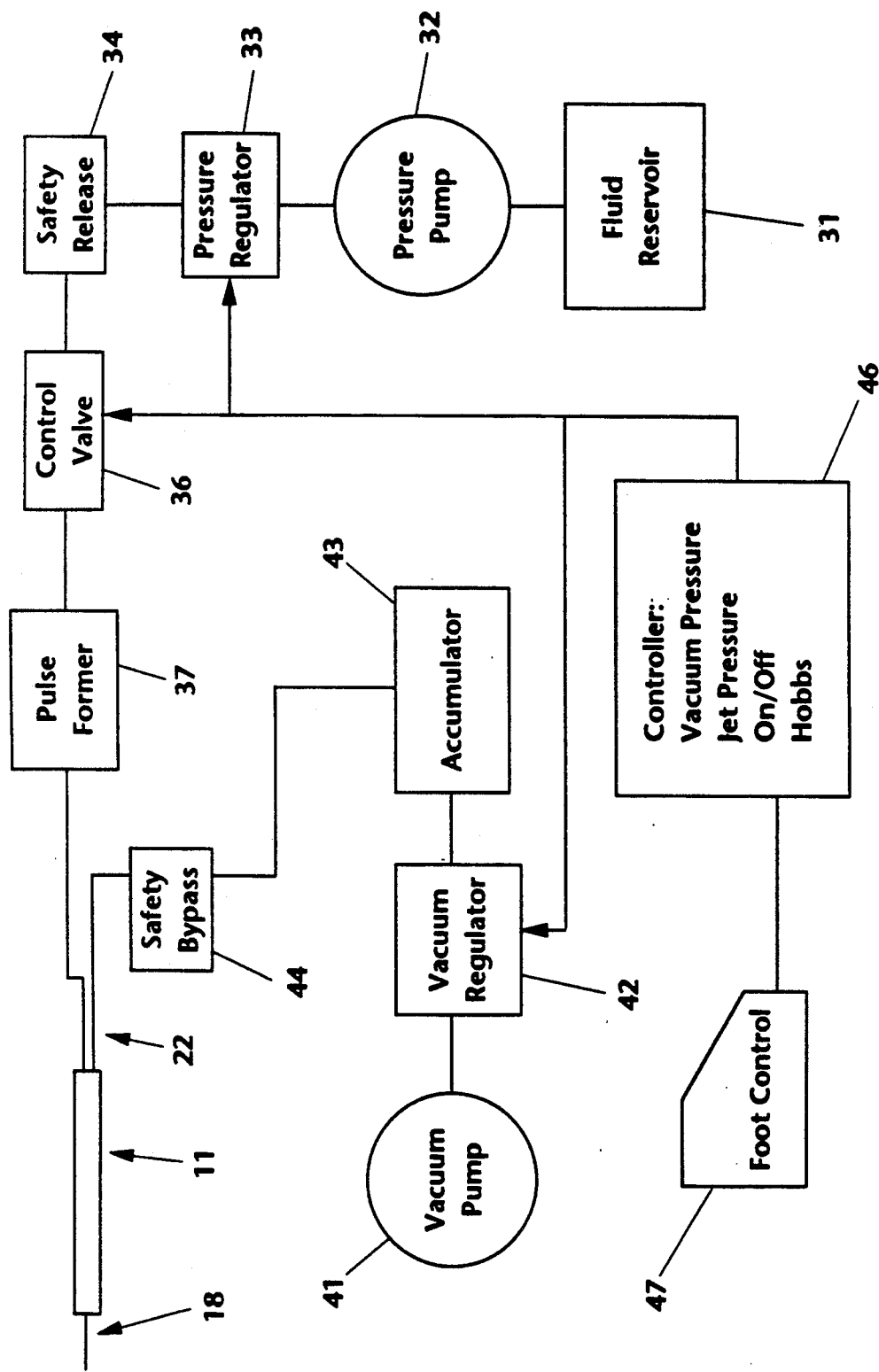
Figure_5

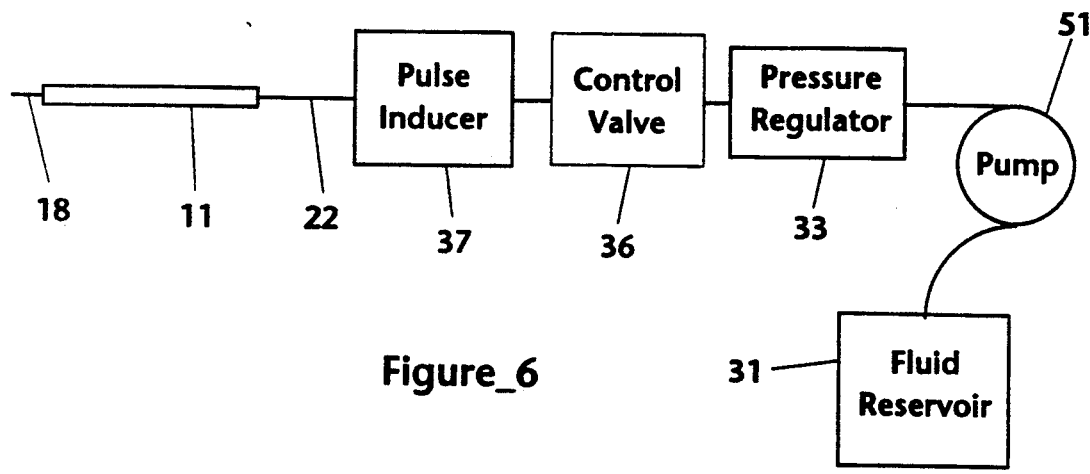
Figure_6
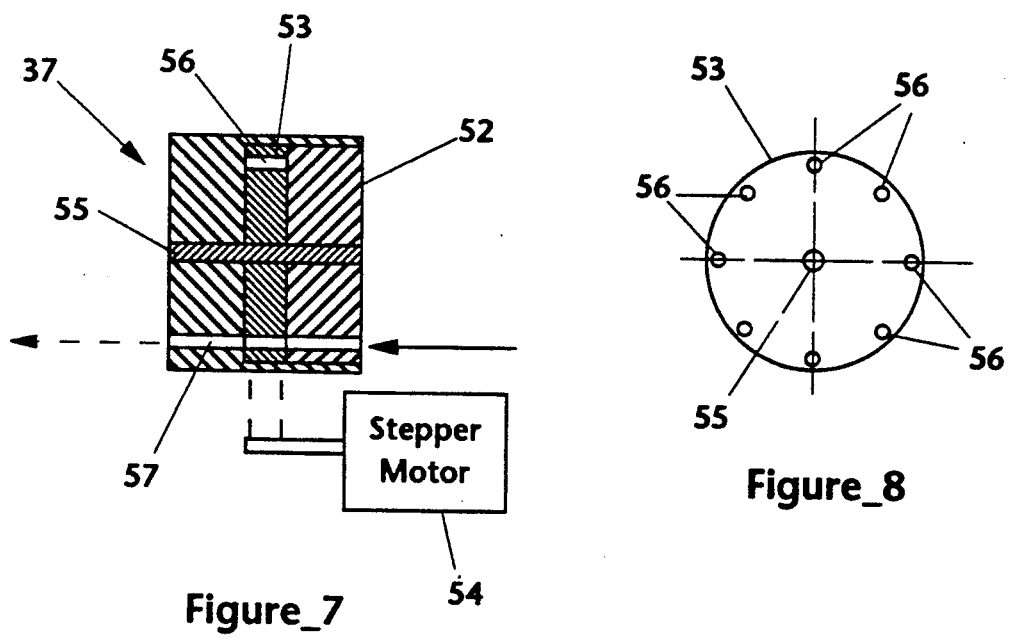
Figure_7
Figure_8

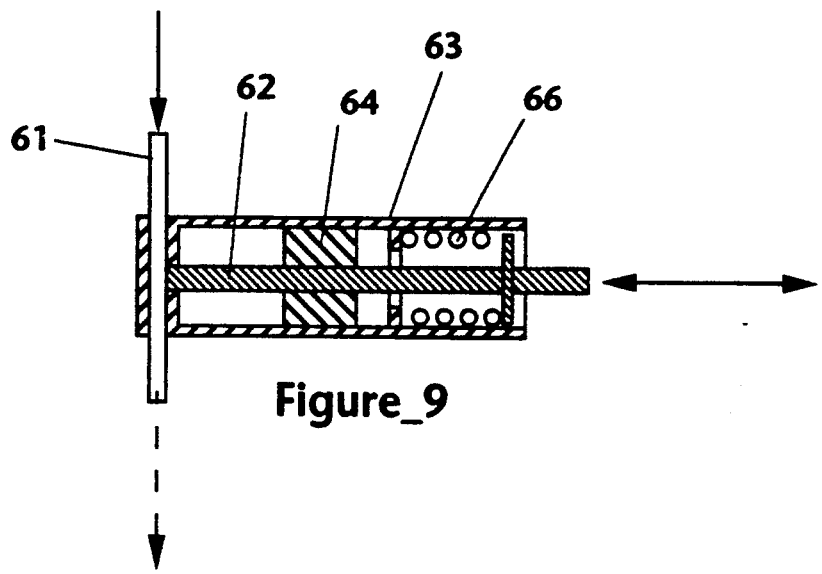
Figure_9
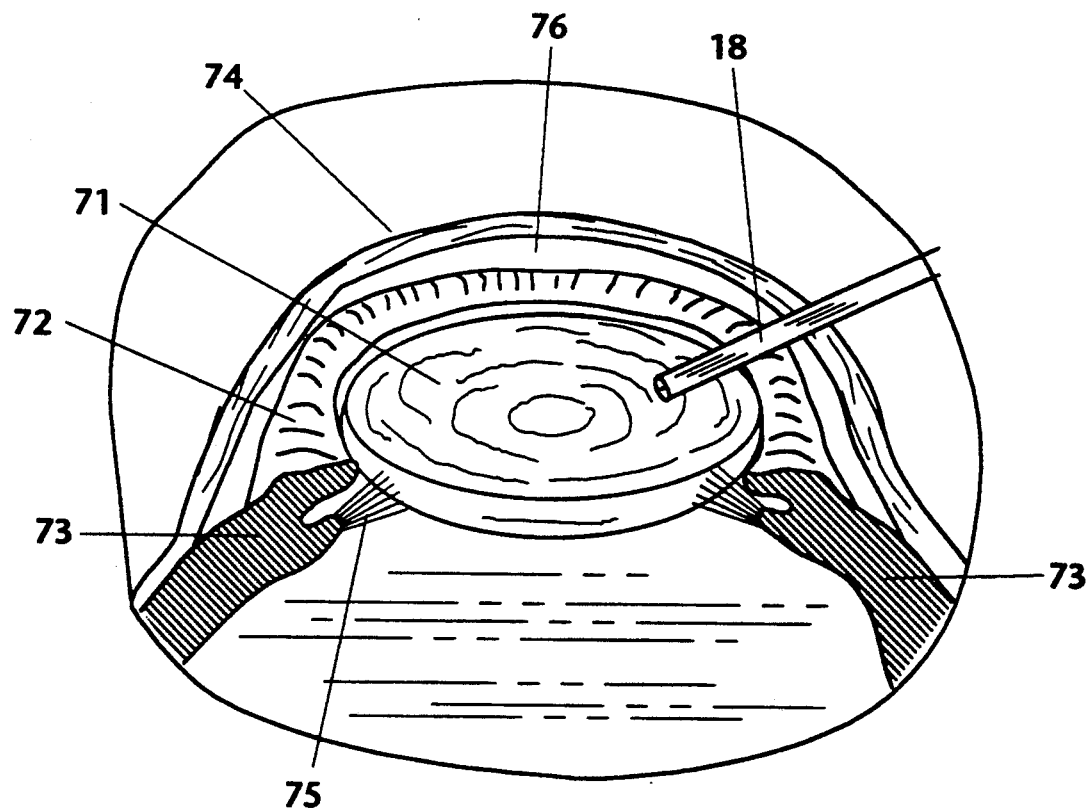
Figure_10

METHOD AND APPARATUS FOR TISSUE EXCISION AND REMOVAL BY FLUID JET

BACKGROUND OF THE INVENTION

The present invention generally relates to excision and removal of tissue in surgical procedures, and more specifically to the use of fluid jet means for excising and removing tissue. In particular, the invention is directed toward the emulsification and removal of the lens of the eye to treat cataracts and similar disorders.

In recent years the treatment of cataracts through surgical techniques has become routine and highly successful. Generally, the affected lens of the eye is removed from its capsule within the eye, and a lens prosthesis is installed within the capsule. Through prudent choice of prosthesis and refractive power, it is often possible to provide normal vision to a patient who would otherwise be sightless.

The step of removing the cataract-beating lens was originally found to be difficult when performed by traditional surgical techniques. An incision sufficiently large to permit removal of the hard lens as a unitary object creates trauma to the delicate ocular structures, and results in prolonged recovery and patient discomfort. Moreover, it is generally considered vital to maintain the integrity of the posterior wall of the lens capsule to prevent the fibrous vitreous humour of the posterior chamber from invading the anterior chamber of the eye and affecting the iris and other important structures. The capsule is easily damaged by traditional surgical techniques.

As a result of these constraints, new techniques such as micro-cutters and acoustic emulsification have been introduced to increase the safety of the cataract removal procedure and decrease the trauma to the eye. In the former technique an inner needle reciprocates within an outer sheath that includes an intake port; vacuum pressure applied to the inner needle pulls tissue into the port, the end of the needle shears it off, and it is drawn away by the vacuum-induced flow through the needle. In this manner a hard object such as the ocular lens may be cut away incrementally and removed through a small puncture hole. In the latter technique ultrasound energy is directed toward the lens via an acoustic probe to fracture and emulsify the lens, and a vacuum channel then removes the lens detritus.

Although these techniques are generally successful, they also have limitations. Micro-cutters may fail to remove all of the lens tissue, and the instrument itself may puncture the posterior wall of the lens capsule. Likewise, the acoustic probe used in acoustic emulsification is limited in the amplitude of energy it can direct to the lens, and may fail to emulsify all of the lens tissue.

SUMMARY OF THE INVENTION

The present invention generally comprises a method and apparatus for the excision and removal of tissue, such as the lens of the eye. The invention employs a fluid jet to fracture and emulsify the lens tissue, and vacuum aspiration to remove the lens tissue as it is emulsified.

The apparatus of the invention includes a pencil-like handpiece having a probe assembly extending from the distal end thereof. The probe assembly includes an inner jet tube which is adapted to direct a high pressure jet of fluid toward a tissue target, and an outer concentric aspiration tube that is adapted to aspirate fluid and remove it from the target area. The jet tube is recessed proximally within the concentric aspiration tube, and the aspiration tube has an end area significantly larger than the end area of the jet tube. These factors cooperate so that the negative pressure exerted by the aspiration tube creates a suction force that offsets and exceeds the force of the fluid jet.

The jet tube is connected proximally to a fluid pressure system which includes a positive displacement pump, a pressure regulator, safety release, control valve, and a pulse former. Thus the jet tube emits pulses of high pressure fluid that impinge reiteratively on the tissue target, such as the ocular lens. The pulses create shock waves that fracture and emulsify the lens tissue, and the fluid also acts as a solvent to transport the emulsified tissue into the aspiration tube. The aspiration tube is connected proximally to a negative pressure system comprising a vacuum pump, an accumulator, and a vacuum regulator. The handpiece also includes a vacuum bypass port disposed to be selectively occluded by a finger of the surgeon, so that vacuum pressure may be released immediately when needed.

The system also includes a control system which monitors and sets the vacuum pressure, the fluid jet pressure, the pulse rate, and other system parameters. A foot control is provided for the surgeon as an on/off switch that requires no manual input.

BRIEF DESCRIPTION OF THE DRAWING

FIG. 1 is a partially cutaway side elevation of the handpiece assembly of the present invention.

FIG. 2 is an end view taken along line 2—2 of FIG. 1, showing the distal end configuration of the probe assembly.

FIG. 3 is an end view taken along line 3—3 of FIG. 1, showing the proximal connections of the aspiration tube and fluid pressure tube to the handpiece assembly.

FIG. 4 is a magnified perspective view of the distal end of the probe assembly.

FIG. 5 is a functional block diagram of the vacuum aspiration system, fluid pressure system, and control system of the present invention.

FIG. 6 is a functional block diagram of one embodiment of the fluid pressure/pulse former system of the invention.

FIG. 7 is a cross-sectional elevation of one embodiment of the pulse former of the fluid pressure system.

FIG. 8 is a plan view of the rotating disk of the pulse former of FIG. 7.

FIG. 9 is a cross-sectional elevation of another embodiment of the pulse former of the fluid pressure system.

FIG. 10 is a cutaway perspective view of the probe portion of the invention in use removing the lens of the eye.

DESCRIPTION OF THE PREFERRED EMBODIMENT

The present invention generally comprises a method and apparatus for the excision and removal of tissue, such as the lens of the eye. The apparatus of the invention includes a pencil-like handpiece 11, shown in FIG. 1. The handpiece includes a tubular body 12 having a tapered distal end 13 and a proximal end 14 in opposed relationship along a longitudinal axis. A pair of flow channels 16 and 17 extend through the body 12 parallel to the longitudinal axis. Extending distally from the end 13 is a cannula probe assembly 18. As shown in FIGS. 2 and 4, the probe assembly 18 comprises an inner tube 19 and a concentric outer tube 21. The diameter of the inner tube 19 is significantly smaller than the diameter of the outer tube 21. For example, the inner tube may comprise an 18 gauge needle, and the outer tube may comprise an 11 gauge needle. As a result, the area of the opening of the outer tube 21 is significantly greater than the area of the opening of the inner tube (i.e., equal to or greater than approximately 5 times the area). Furthermore, the distal end of the inner tube 19 is recessed proximally with respect to the distal end of the outer tube 21 on the order of approximately 1 mm.

The inner tube 19 is connected directly to the flow channel 16 in the tubular body 12. The proximal end of the flow channel 16 is connected to a tube assembly 22 that is connected to a controlled fluid pressure source. The outer tube 21 is connected to a distal flow space 23 within the distal end 13, and the distal flow space is connected to the flow channel 17. The flow channel 17 joins a proximal flow space 24 at the end 14 which is connected through the tube assembly 22 to a controlled negative pressure source. (The tube assembly 22 may comprise concentric tubes, as shown in FIG. 3, or adjacent tubes joined to the end assembly 14.) Thus the handpiece 11 is configured to deliver a fluid jet from the distal end of the inner tube 19 while simultaneously providing aspiration of fluid and flowable substances through the distal end of the outer tube 21.

In addition, the tubular body 12 includes a port 26 adjacent to the distal end 13 that extends to the distal flow space 23. The port 26 is positioned to be occluded by a fingertip of the hand that wields the handpiece, so that negative pressure will be delivered to the tube 21. Opening the port 26 by lifting the occluding fingertip permits ambient air inflow that eliminates the aspiration effect at the distal end of the tube 21. The port 26 thus comprises a safety release feature for instantaneous interruption of the aspiration function.

The apparatus also includes systems for supplying negative (vacuum) pressure and fluid under pressure to the handpiece, as well as a control system for the vacuum and fluid pressure systems. With regard to FIG. 5, the fluid pressure system includes a fluid reservoir 31 connected to a positive displacement pressure pump 32. The output of the pump 32 is fed through a selectively variable pressure regulator 33 and a safety pressure release 34 to an on-off control valve 36. The output of the control valve is connected to a pulse forming device 37, as described below, and thence to the tubing assembly 22 and the handpiece 11. The pulse rate may be set from zero to continuous flow, the rate depending on the density, fibrosity, and resiliency of the tissue.

It is significant that the fluid pressure system is arranged to deliver pulses of high pressure fluid to the cannula probe 18; the pulsatile nature of the fluid jet emitted from the cannula induces shock waves in the target tissue and aids in fracturing and emulsifying the tissue to facilitate aspiration and removal. In addition, the fine stream of fluid under pressure creates a tissue incising effect at a rate dependent on the nature of the tissue and the level of fluid pressure. The fluid pressure system is adapted to provide pressure in the range of 0–300 kp/mm. The optimum operating range is 10 to 15 psi, depending on the composition of the tissue.

The vacuum pressure system includes a vacuum pump 41 connected through a selectively variable regulator 42 to an accumulator 43. The accumulator may comprise a standard aspiration collection bottle known in the medical arts, in which the bottle defines a plenum volume maintained at a negative pressure by the regulator 42 and pump 41. An aspiration tubing line extends from the accumulator 43 through a safety bypass 44 to the handpiece 11. The system is arranged to provide a negative pressure in the range of 0–24 inches Hg for optimum aspiration effect.

The control system comprises sensor/actuator devices connected to the fluid pressure line and the vacuum accumulator to monitor and adjust these pressures to maintain optimal, adjustable levels. The control system also includes a logic system or microprocessor under software control to monitor the pressure systems and to actuate the control valve 36 upon demand. A footswitch control 47 is connected to the control system 46 to enable the surgeon to turn on and off the fluid jet and vacuum aspiration systems without manual input. The control system 46 also includes a hobbsmeter; i.e., a device for displaying elapsed operating time, as well as vacuum pressure, fluid jet pressure, and pulse rate.

As shown in FIG. 6, the fluid pressure pump may comprise a peristaltic pump 51 to generate fluid pressure without risk of excessive pressure or volume. The pressure pump may also comprise a positive displacement piston pump, a diaphragm pump, a gear pump, or the like, all known in the prior art.

With regard to FIGS. 7 and 8, one embodiment of the pulse forming device 37 described above comprises a body 52 having a chamber formed therein, and a disk 53 disposed within the chamber and mounted on a pivot shaft 55 for rotation thereabout. The body 52 includes a flow channel 57 extending therethrough parallel to the shaft 55, and the disk 53 includes a plurality of holes 56 extending through and spaced about the periphery. The disk 53 blocks the flow channel and prevents fluid passage therethrough. The holes 56 are positioned with respect to the shaft 55 and the flow channel 57 so that the holes 56 are brought into registration with the flow channel 57 sequentially and reiteratively, so that a brief period of fluid flow is established by the passage of each hole 56 past the channel 57. As a result, rotation of the disk 53 results in a continuous train of fluid pulses through the channel 57. A stepper motor 54 is coupled to the disk 53, and a variable speed drive system coupled to the stepper motor enables a selectively variable pulse rate.

A further embodiment of the pulse forming device 37, shown in FIG. 9, includes a valve body 63 having a flow channel 61 extending therethrough. A valve stem 62 is reciprocally translatable in the valve body, and the end of the valve stem is disposed to block the channel 61 when translated distally. A solenoid actuator 64 is disposed to drive the valve stem distally, and a spring 66 is mounted between the valve body and the valve stem to return the valve stem proximally. The solenoid is connected to an electrical pulse source having a variable pulse rate, so that the valve stem may be driven at a selected rate to interrupt the flow channel 61 and create a train of fluid pulses.

It should be noted that the operating parameters of the invention, including pulse rate, jet pressure, and vacuum pressure, may be varied to optimize desired effects such as cutting and emulsifying for various types of tissue. These parameters may be determined empirically.

With regard to FIG. 10, a preferred use of the apparatus comprises removal of the ocular lens 71 for the purpose of correcting visual problems due to cataracts or other defects in the lens. The lens 71 is circumscribed by the iris 72 and the ciliary muscle 73 which is secured to the lens by the ciliary zonular fibers 75. The cornea 74 extends across the anterior medial portion of the eye, and the anterior chamber 76 of the eye is defined between the cornea and the iris and lens. The lens is surrounded by a capsule (not shown).

To remove the lens 71, the cannula probe 18 of the invention is extended through a small incision or puncture hole beyond the margin of the iris, through the lens capsule to impinge on the lens itself. At this point the fluid pressure and aspiration systems are actuated by the foot control 47, and the cannula probe 18 begins to emitting high pressure pulses of fluid that impinge on a target zone at the lens surface. The pulsed fluid jet from the tube 19 incises the laminar layers of the lens, and the shock waves induced in the target zone by the pulse action cause the lens tissue to emulsify in the fluid. The emulsified tissue and fluid are aspirated by the outer tube 21 and removed from the eye. As tissue is removed from the target zone a fresh target surface is exposed; as the pulsed fluid jet and aspiration continue, the lens tissue is incrementally but rapidly removed. After removal of the entire lens, a lens prosthesis may be inserted and anchored in its place to provide proper optical correction to optimize visual acuity.

The present invention provides several advantages over prior art devices such as ultrasound phako-emulsifiers. For example, the pulsed jet of the invention is highly directional, so that the cutting and emulsifying effects may be applied precisely to a tissue target. In contrast, ultrasound energy can cause unintended damage to tissue adjacent to a target, due to reflection, acoustic conduction and resonance, and the like. These acoustic effects can be unpredictable due to unforeseen variations in tissue composition. This danger has caused many surgeons to be reluctant to use ultrasonic devices in delicate surgery. Furthermore, the apparatus of the invention is generally less costly than ultrasound devices, and thus promises to lower the cost of surgical procedures such as cataract removal.

What is claimed:

1. An apparatus for removing tissue from a tissue target, including;
   jet means for directing a high pressure fluid jet at the tissue target;
   pressure means for supplying said jet means with high pressure fluid;
   aspiration means for aspirating fluid and tissue from said tissue target;
   handpiece means for directing said jet means and said aspiration means at the tissue target, said handpiece means including a pencil-like body having a distal end and a proximal end, a substantially rigid cannula probe extending from said distal end;
   said jet means including a jet tube in said substantially rigid cannula probe, and said aspiration means including an aspiration tube in said cannula probe, said aspiration tube disposed concentrically about said jet tube;
   said jet tube including a distal output end and said aspiration tube including a distal intake end, and said distal output end of said jet tube is recessed proximally within said distal intake end of said aspiration tube.

2. The apparatus of claim 1, wherein said pressure means includes a pressure channel extending through said body from said proximal end to said distal end.

3. The apparatus of claim 2, wherein said aspiration means includes a negative pressure channel extending through said body from said proximal end to said distal end.

4. The apparatus of claim 3, wherein said aspiration means includes a safety release port in said handpiece, said safety release port extending from said negative pressure channel to the ambient atmosphere, said safety port being disposed to be selectively occluded by manual action.

5. The apparatus of claim 3, further including tubing assembly means joined to said proximal end of said body and connected to supply high pressure fluid to said pressure channel and negative pressure to said negative pressure channel.

6. A method for removal of the ocular lens from the human body, comprising the steps of:
   providing a cannula probe having a jet tube and an aspiration tube;
   inserting the cannula probe into the lens capsule and directing the cannula probe at the lens tissue;
   directing a jet of high pressure fluid from the jet tube toward the lens tissue to excise and emulsify the lens tissue while simultaneously applying negative pressure to said aspiration tube for aspirating fluid and lens tissue through said aspiration tube from the lens capsule;
   pulsating the jet of high pressure fluid to enhance the lens emulsifying effect of the fluid jet; and,
   positioning the jet tube recessed from the intake end of the aspiration tube and concentrically within the aspiration tube.

7. The method of claim 6, wherein said aspiration tube includes an intake opening, and said negative pressure is controlled so that the suction force exerted toward the lens tissue at the intake opening offsets and exceeds the force of the fluid jet.

* * * * *